United States Patent [19]

Hsieh

[11] Patent Number: 5,546,439
[45] Date of Patent: Aug. 13, 1996

[54] SYSTEMS, METHODS AND APPARATUS FOR INCREMENTALLY RECONSTRUCTING OVERLAPPED IMAGES IN A CT SYSTEM IMPLEMENTING A HELICAL SCAN

[75] Inventor: Jiang Hsieh, Waukesha, Wis.

[73] Assignee: General Electric Company, Milwaukee, Wis.

[21] Appl. No.: 552,264

[22] Filed: Nov. 2, 1995

[51] Int. Cl.⁶ ........................................................ A61B 6/03
[52] U.S. Cl. .................... 378/15; 378/901; 364/413.18
[58] Field of Search ................. 378/15, 94; 364/413.18

[56] References Cited

U.S. PATENT DOCUMENTS

| | | | |
|---|---|---|---|
| 4,144,507 | 3/1979 | Wagner | 364/413.18 |
| 4,580,219 | 4/1986 | Pelc et al. | 364/413.21 |
| 4,821,210 | 4/1989 | Rumbaugh | 395/121 |
| 5,047,931 | 9/1991 | Lin | 364/413.21 |
| 5,233,518 | 8/1993 | King et al. | 364/413.18 |
| 5,253,171 | 10/1993 | Hsiao et al. | 364/413.19 |
| 5,265,142 | 11/1993 | Hsieh | 378/4 |
| 5,270,923 | 12/1993 | King et al. | 364/413.13 |
| 5,491,735 | 2/1996 | Hsieh | 378/15 |

OTHER PUBLICATIONS

Crawford et al., Computed Tomography with Simultaneous Patient Translation, Med. Phys. 17(6), Nov./Dec. 1990, pp. 967–982.

*Primary Examiner*—David P. Porta
*Assistant Examiner*—David Vernon Bruce
*Attorney, Agent, or Firm*—John S. Beulick; John H. Pilarski

[57] ABSTRACT

The present invention, in one form, is a system for producing incremental tomographic images of an object from projection data acquired in a helical scan. The system creates base image data arrays from the projection data. An interpolation algorithm is then applied to the base image data arrays to generate overlapped, or incremental, tomographic images.

18 Claims, 1 Drawing Sheet

SYSTEMS, METHODS AND APPARATUS FOR INCREMENTALLY RECONSTRUCTING OVERLAPPED IMAGES IN A CT SYSTEM IMPLEMENTING A HELICAL SCAN

FIELD OF THE INVENTION

This invention relates generally to computed tomography (CT) imaging and more particularly, to the incremental reconstruction of overlapped images from projection data acquired from a helical scan.

BACKGROUND OF THE INVENTION

In at least one known CT system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the tan beam yields projection data from which images in each prescribed slice may be reconstructed. Image reconstruction algorithms which may be utilized in reconstructing an image from data obtained in a helical scan are described in C. Crawford and K. King, "Computed Tomography Scanning with Simultaneous Patient Translation," Med. Phys. (716), November/December 1990, and in U.S. patent application Ser. No. 08/362,247, Helical Interpolative Algorithm For Image Reconstruction In A CT System, filed Dec. 22, 1994 and assigned to the present assignee. The known algorithms may generally be classified as Helical Extrapolative (HE) or Helical Interpolative (HI) algorithms. These algorithms typically apply a weighting function to the projection data in order to reconstruct an image. This weighting function is generally based on both the fan angle and view angle.

To achieve maximum observability of an object of interest, it is known to generate overlapping images so that one of the images centers around the object of interest. Constructing overlapping images, which typically are different views of the object of interest, is generally referred to as incremental reconstruction. Incremental reconstruction techniques are described, for example, in M. Remy-Jardin et al., "Chest evaluation with Use of Spiral Volumetric CT with the Single Breathold Technique," RSNA '91, pp. 273, November 1991, P. Costello et al., "Spiral CT of the Thorax with Small Volumes of Contrast Material: A Comparative Study" RSNA '91, pp. 274, November 1991, and D. E. Duppey, "Spiral CT of the Pancreas: Comparative Study," RSNA '91, pp. 260, November 1991.

In one known incremental reconstruction technique, an image, sometimes referred to as the "seed" image, which is common to all overlapping images is generated. When a new projection is obtained, its contribution is added to the seed image and a view corresponding to the same angular position (360° apart) is subtracted from the seed image. This approach permits images to be continuously updated to generate overlapping reconstructions.

For an axial scan in which the patient remains stationary during the entire data acquisition, the amount of computation and computation time are reduced by using a seed image since a major portion of the scan data does not have to be re-processed for each view. However, with respect to a helical scan, the seed image technique is slow and cumbersome. Specifically, with helical scan data, a weighting function is applied to the projection data prior to the filtering and backprojection process. The weighting function, as explained above, is a function of both the fan angle and the view angle.

Therefore, in a helical scan context, a new image cannot be generated by simply deleting one view and adding another since the contributions from the remaining views need to be adjusted or updated, i.e., weighted. Each overlapped image therefore must be generated independently, and the amount of time required to generate overlapped images linearly increases with the number of images to be generated.

It would be desirable, of course, to reconstruct overlapping images from helical scan data without having to independently generate each overlapped image, yet substantially maintain image quality. It also is desirable to reduce the processing and total time required to reconstruct such overlapping images from helical scan data to prevent any undesirable delays.

SUMMARY OF THE INVENTION

These and other objects may be attained in a system which, in one embodiment, implements an incremental reconstruction algorithm for helical scan data which does not require independent generation of each overlapped image. Particularly, in accordance with one embodiment of the present invention, and rather than utilizing a seed image as in an axial scan, base images are generated. The locations of base images generated are determined using, for example, the well known Nyquist sampling theory. Once the base image data is generated, such base image data is utilized to generate overlapped images. Specifically, an interpolation algorithm, such as a fourth order LaGrange algorithm, may be utilized to generate the overlapping image data.

Using the incremental reconstruction algorithm described above enables reconstruction of overlapping images from helical scan data without requiring that each image be independently generated. As a result, and with helical scan data, the processing time needed to reconstruct overlapped images is reduced as compared to the processing time needed by the "seed" image algorithm described above. In addition, the present reconstruction algorithm is believed to maintain image quality. Moreover, the present reconstruction algorithm also reduces streaks and artifacts in three dimensional (3 D) or multi-planar reformat (MPR) images.

DETAILED DESCRIPTION OF THE DRAWINGS

Figure 1:
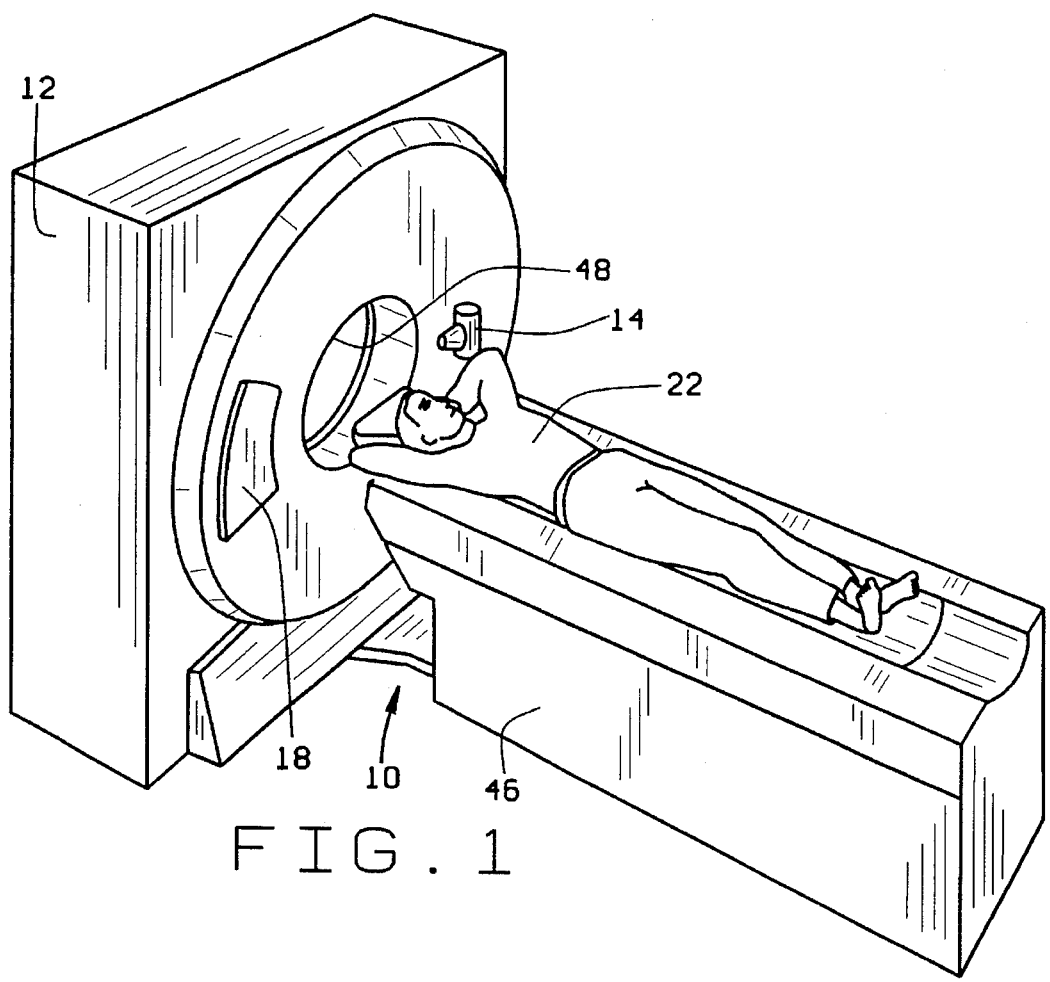
FIG. 1 is a pictorial view of a CT imaging system.
Figure 2:
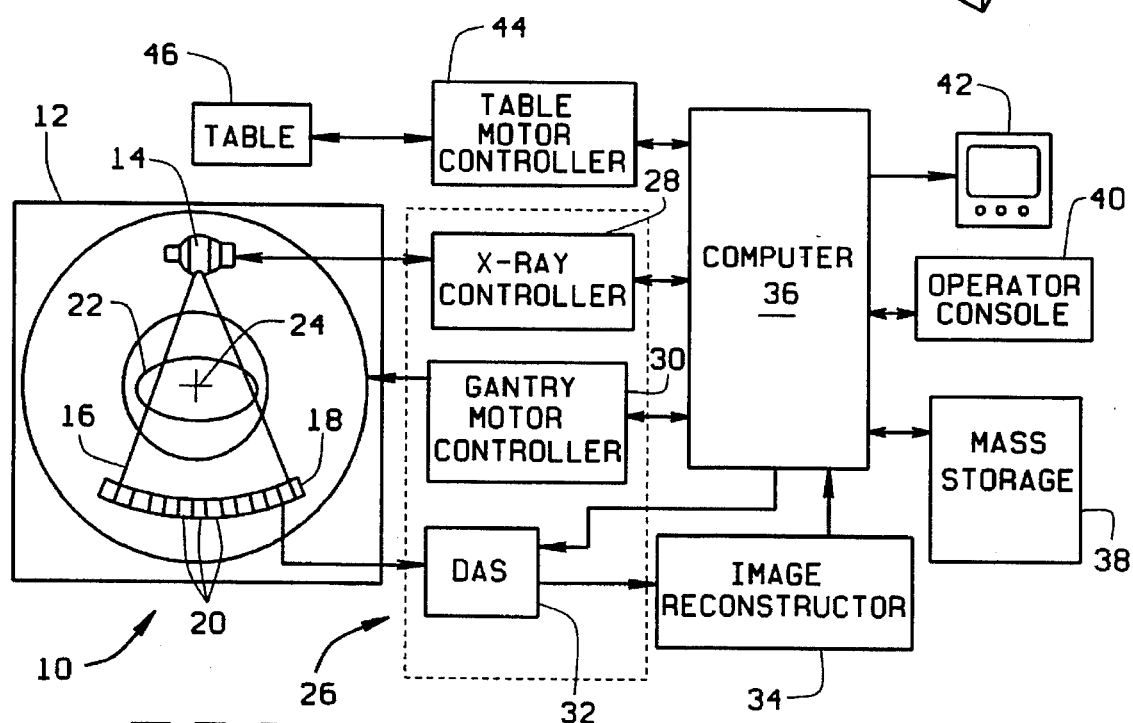
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Preferably, the reconstructed image is stored as a data array.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

For purposes of the following discussion, an Xmm by Xmm scan refers to scanning an object of interest using an Xmm collimator aperture at a 1:1 helical pitch, wherein helical pitch is the ratio of table 46 movement in one rotation of the x-ray source 14 to the slice width defined by the source collimator.

With respect to incremental reconstruction, and in accordance with one embodiment of the present invention, subsequent to generation of image data from helical scan projection data by image reconstructor 34, and subsequent to selection of an object of interest, base image data for the object of interest is identified by computer 36. The locations of base images identified by computer 36 for an object is determined, for example, by using the well known Nyquist sampling theory. The Nyquist sampling theory provides that the required sampling rate should be twice of the maximum frequency. For example, where the object of interest is to be scanned using a 3 mm by 3 mm helical scan and images are to be reconstructed with a $2\pi$ extrapolative algorithm, the maximum frequency content (the first zero crossing point) is only 3 line pairs per centimeter (LP/cm). Base image data should thus be reconstructed at 1.5 mm increments (50% overlap). Similarly, if an object of interest is to be scanned using a 10 mm by 10 mm scan and images are to be reconstructed with a $2\pi$ extrapolative algorithm, the Nyquist sampling theory requires that the base image data should be reconstructed every 5 mm (50% overlap). Subsequent to identifying the locations of the base images, base image data is generated for the identified locations.

Once the base image data is generated, overlapping images are reconstructed using the base image data. Particularly, overlapping images are generated by performing interpolations using the base image data. Interpolation of the base image data may be performed, for example, using a LaGrange or cubic splines interpolation algorithm. Other interpolation algorithms could, of course, be utilized.

As an example, with respect to reconstructing overlapping images using a fourth order LaGrange interpolating algorithm, $x_k$ and $y_k$, where k=1, 2, 3, 4, denote the nominal positions and the actual data of four base images. $\xi$ denotes the location between $x_2$ and $x_3$ where an interpolated image is to be generated. The new image data, $y_\xi$, can be obtained by:

$$y_\xi = \sum_{i=1}^{4} w_{i\xi} y_i \qquad (1)$$

where $$w_{1\xi} = \frac{(\xi - \chi_2)(\xi - \chi_3)(\xi - \chi_4)}{(\chi_1 - \chi_2)(\chi_1 - \chi_3)(\chi_1 - \chi_4)}$$

$$w_{2\xi} = \frac{(\xi - \chi_1)(\xi - \chi_3)(\xi - \chi_4)}{(\chi_2 - \chi_1)(\chi_2 - \chi_3)(\chi_2 - \chi_4)}$$

$$w_{3\xi} = \frac{(\xi - \chi_1)(\xi - \chi_2)(\xi - \chi_4)}{(\chi_3 - \chi_1)(\chi_3 - \chi_2)(\chi_3 - \chi_4)}$$

$$w_{4\xi} = \frac{(\xi - \chi_1)(\xi - \chi_2)(\xi - \chi_3)}{(\chi_4 - \chi_1)(\chi_4 - \chi_2)(\chi_4 - \chi_3)}.$$

Once the image data for the new view is determined as explained above, the new image can be displayed.

As explained above, and in a helical scan context, new images may be displayed without requiring that the new images be independently generated. Rather, the new image data for the new image is determined by using the base image data and well known interpolation algorithms. Further, with respect to helical scanning, the image quality of overlapping images generated in accordance with the present algorithm utilizing the fourth order LaGrange interpolation is believed to be about the same as the image quality of overlapping images generated using a seed image. In addition, with helical scan data, the reconstruction speed for generating each overlapping image is believed to be significantly increased using the algorithm described above as compared to the speed for reconstructing overlapping images using a seed image.

From the preceding description it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Also, as explained above, interpolation algorithms other than a fourth order LaGrange algorithm may be utilized. Accordingly, the spirit and scope of the invention are to be limited only by the terms of the appended claims.

What is claimed is:

1. A system for producing incremental tomographic images of an object from projection data acquired in a helical scan, said tomographic image system configured to:
   (a) create base image data arrays from the projection data; and
   (b) generate overlapped image data, utilizing an interpolation algorithm, from the data in the base image data arrays.

2. A system in accordance with claim 1 wherein to create base image data arrays, the system is configured to:
   identify locations of base images; and
   generate base image data arrays for the identified locations.

3. A system in accordance with claim 2 wherein the locations of base images are determined in accordance with the Nyquist sampling theory.

4. A system in accordance with claim 1 wherein the interpolation algorithm is a LaGrange interpolative algorithm.

5. A system in accordance with claim 4 where the LaGrange interpolative algorithm is:

$$y_\xi = \sum_{i=1}^{4} w_{i\xi} y_i$$

where $\xi$ denotes a desired image position;

$y_\xi$ denotes the interpolated image; and $$w_{1\xi} = \frac{(\xi - \chi_2)(\xi - \chi_3)(\xi - \chi_4)}{(\chi_1 - \chi_2)(\chi_1 - \chi_3)(\chi_1 - \chi_4)}$$

$$w_{2\xi} = \frac{(\xi - \chi_1)(\xi - \chi_3)(\xi - \chi_4)}{(\chi_2 - \chi_1)(\chi_2 - \chi_3)(\chi_2 - \chi_4)}$$

$$w_{3\xi} = \frac{(\xi - \chi_1)(\xi - \chi_2)(\xi - \chi_4)}{(\chi_3 - \chi_1)(\chi_3 - \chi_2)(\chi_3 - \chi_4)}$$

$$w_{4\xi} = \frac{(\xi - \chi_1)(\xi - \chi_2)(\xi - \chi_3)}{(\chi_4 - \chi_1)(\chi_4 - \chi_2)(\chi_4 - \chi_3)}.$$

6. A system in accordance with claim 4 wherein to create base, image data arrays, the system is configured to:
   identify locations of base images in accordance with the Nyquist sampling theory; and
   generate base image data arrays for the identified locations.

7. A method for producing a tomographic image of an object from projection data acquired in a helical scan, said method comprising the steps of:
   (a) creating base image data arrays from the projection data; and
   (b) generating overlapped images, utilizing an interpolation algorithm, from the data in the base image data arrays.

8. A method in accordance with claim 7 wherein the interpolation algorithm is a LaGrange algorithm.

9. A method in accordance with claim 8 wherein the LaGrange algorithm is:

$$y_\xi = \sum_{i=1}^{4} w_{i\xi} y_i$$

where $\xi$ denotes a desired image position;

$y_\xi$ denotes the interpolated image; and $$w_{1\xi} = \frac{(\xi - \chi_2)(\xi - \chi_3)(\xi - \chi_4)}{(\chi_1 - \chi_2)(\chi_1 - \chi_3)(\chi_1 - \chi_4)}$$

$$w_{2\xi} = \frac{(\xi - \chi_1)(\xi - \chi_3)(\xi - \chi_4)}{(\chi_2 - \chi_1)(\chi_2 - \chi_3)(\chi_2 - \chi_4)}$$

$$w_{3\xi} = \frac{(\xi - \chi_1)(\xi - \chi_2)(\xi - \chi_4)}{(\chi_3 - \chi_1)(\chi_3 - \chi_2)(\chi_3 - \chi_4)}$$

$$w_{4\xi} = \frac{(\xi - \chi_1)(\xi - \chi_2)(\xi - \chi_3)}{(\chi_4 - \chi_1)(\chi_4 - \chi_2)(\chi_4 - \chi_3)}.$$

10. A method in accordance with claim 7 wherein creating base image data arrays comprises:
    identifying the locations of base images; and
    generating base image data arrays for the identified locations.

11. A method in accordance with claim 10 wherein identifying the locations of base images is performed in accordance with the Nyquist sampling theory.

12. A method in accordance with claim 10 wherein the interpolation algorithm is a LaGrange algorithm.

13. A method in accordance with claim 12 wherein the LaGrange algorithm is:

$$y_\xi = \sum_{i=1}^{4} w_{i\xi} y_i$$

where $\xi$ denotes a desired image position;

$y_\xi$ denotes the interpolated image; and $$w_{1\xi} = \frac{(\xi - \chi_2)(\xi - \chi_3)(\xi - \chi_4)}{(\chi_1 - \chi_2)(\chi_1 - \chi_3)(\chi_1 - \chi_4)}$$

$$w_{2\xi} = \frac{(\xi - \chi_1)(\xi - \chi_3)(\xi - \chi_4)}{(\chi_2 - \chi_1)(\chi_2 - \chi_3)(\chi_2 - \chi_4)}$$

$$w_{3\xi} = \frac{(\xi - \chi_1)(\xi - \chi_2)(\xi - \chi_4)}{(\chi_3 - \chi_1)(\chi_3 - \chi_2)(\chi_3 - \chi_4)}$$

$$w_{4\xi} = \frac{(\xi - \chi_1)(\xi - \chi_2)(\xi - \chi_3)}{(\chi_4 - \chi_1)(\chi_4 - \chi_2)(\chi_4 - \chi_3)}.$$

14. A computed tomography apparatus, comprising:
    a gantry having an x-ray source and a detector;
    a data acquisition system coupled to the detector; and
    a computer coupled to the data acquisition system, the computer configured to identify, for an object of interest, locations of base images, create base image data arrays for the identified locations, and generate overlapped images, utilizing an interpolation algorithm, from data stored in the base image data arrays.

15. A computed tomography apparatus in accordance with claim 14 wherein the computer is further configured to identify locations of base images in accordance with the Nyquist sampling theory.

16. A computed tomography apparatus in accordance with claim 14 wherein the interpolation algorithm is a LaGrange algorithm.

17. A computed tomography apparatus in accordance with claim 16 wherein the LaGrange algorithm is:

$$y_\xi = \sum_{i=1}^{4} w_{i\xi} y_i$$

where $\xi$ denotes a desired image position;

$y_\xi$ denotes the interpolated image; and $$w_{1\xi} = \frac{(\xi - \chi_2)(\xi - \chi_3)(\xi - \chi_4)}{(\chi_1 - \chi_2)(\chi_1 - \chi_3)(\chi_1 - \chi_4)}$$

$$w_{2\xi} = \frac{(\xi - \chi_1)(\xi - \chi_3)(\xi - \chi_4)}{(\chi_2 - \chi_1)(\chi_2 - \chi_3)(\chi_2 - \chi_4)}$$

$$w_{3\xi} = \frac{(\xi - \chi_1)(\xi - \chi_2)(\xi - \chi_4)}{(\chi_3 - \chi_1)(\chi_3 - \chi_2)(\chi_3 - \chi_4)}$$

$$w_{4\xi} = \frac{(\xi - \chi_1)(\xi - \chi_2)(\xi - \chi_3)}{(\chi_4 - \chi_1)(\chi_4 - \chi_2)(\chi_4 - \chi_3)}.$$

18. A computed tomography apparatus in accordance with claim 16 wherein the computer is further configured to identify locations of base images in accordance with the Nyquist sampling theory.

* * * * *